United States Patent [19]
Gleichenhagen et al.

[11] 3,987,000
[45] Oct. 19, 1976

[54] SPRAYABLE POLYMER COMPOSITION

[75] Inventors: Peter Gleichenhagen, Hamburg;
Dietrich Schulte, Pinneberg;
Günther Bonitz, Hamburg, all of
Germany

[73] Assignee: Beiersdorf Aktiengesellschaft,
Germany

[22] Filed: Aug. 29, 1974

[21] Appl. No.: 501,559

[30] Foreign Application Priority Data
Aug. 31, 1973 Germany............................ 2343923

[52] U.S. Cl. ............................ 260/31.2 R; 128/155;
128/156; 128/334 R; 260/32.8 R; 260/33.4
R; 260/33.6 UA; 260/33.8 UA; 526/324;
526/325
[51] Int. Cl.² ..................... A61L 15/00; C08K 5/01;
C08K 5/04; C08K 5/10
[58] Field of Search ....... 260/80.81, 31.2 R, 78.5 R,
260/80.8, 32.8 R, 33.4 R, 33.6 UA, 33.8 UA;
128/155, 156, 334 R; 526/324, 325

[56] References Cited
UNITED STATES PATENTS

| | | |
|---|---|---|
| 2,949,443 | 8/1960 | Merriam et al. .................... 128/156 |
| 3,305,511 | 2/1967 | Gander ............................. 260/33.2 |
| 3,453,245 | 7/1969 | Glavis ............................. 260/78.5 R |
| 3,577,516 | 5/1971 | Gould et al. ...................... 128/155 |
| 3,847,155 | 11/1974 | Bernaola ........................... 128/344 |

*Primary Examiner*—Allan Lieberman
*Attorney, Agent, or Firm*—Bierman & Bierman

[57] ABSTRACT

A polymer composition is disclosed which can be sprayed or otherwise thinly coated on an open wound to serve as a protective bandage. The composition comprises:

a. 10 to 30% by weight of isobutene relative to total monomer weight;

b. 5 to 85% by weight of total monomer of one or more esters of acrylic or methacrylic acid and one or more normal or branched, monovalent, primary or secondary aliphatic alcohols having 1–4 carbon atoms; and c. 5 to 85% by weight of total monomer of one or more maleic acid monoalkyl esters having 1–12 carbon atoms in the monoalkyl portion of the molecule.

8 Claims, No Drawings

SPRAYABLE POLYMER COMPOSITION

This application claims the priority of German application 23 43 923 filed Aug. 31, 1973.

The present invention concerns a film-forming polymer composition, especially such as can be sprayed from aerosol containers. It is sprayed on or otherwise applied in thin layers to a cut, abrasion, or surgical wound that is to be bandaged. After the solvent evaporates, a thin, coherent film forms, which covers the site of injury.

In addition to using textile bandaging materials and adhesive bandages (plasters) to cover wounds, the uses of which are generally connected with a series of disadvantages, it is known that thin, transparent, colorless films with sufficient water vapor permeability can be used. They are formed locally by applying or spraying a polymer solution of appropriate composition onto the wounded area, and by evaporating the solvent. They are capable of adapting themselves to all skin movements at the injured site because of their elasticity and flexibility.

Such polymer solutions, which form a film over the injured site that closes the wound area against the outside, can have quite varying compositions. They are also called "liquid bandaging materials" or "liquid plasters". Such solutions are preferably packaged in aerosol containers together with a propellant and find commercial use in this way. When required, they can be sprayed onto the wound by activating a valve button.

These film-forming, sprayable solutions are usually formed in volatile, non-toxic organic solvents such as ethyl acetate, methylene chloride, chloroform, acetone, ethanol, or their mixtures, with or without the addition of surgical spirits. To produce these solutions various polymers of acrylic and methacrylic acid esters, such as polymethyl methacrylate, polyethyl methacrylate, poly-2-ethoxy ethyl methacrylate, or their mixtures have hitherto been used (DT-AS1 008 874, DT-AS 1 253 414, US-PS 2 949 443). Since these polymers, when used to produce a wound bandage, frequently yielded brittle films which tore easily, it was necessary to remove this undesired effect by amalgamating softeners. For this purpose, synthetic softeners, such as sebacates and phthalates, were suggested, in addition to esters of fatty acids. Besides using polymethacrylates and polyacrylates or their copolymers, plasticized cellulose - aceto-butyrate is also known for this purpose (GB-PS 836 520). Further polymers and polymer mixtures which have been suggested as essential components of film-forming, sprayable solutions to produce wound bandages are vinyl acetate/vinyl chloride mixtures and ethyl cellulose with various additives (DT-AS 1 077 382), polyvinylpyrrolidone (US-PS 3 073 794), as well as copolymers of acrylates and methacrylates, with selected monomers such as n-tert. butylacrylamide (US-PS 3 413 254), or β-dimethylaminoethylmethacrylate or tert. butylamino-ethyl-methacrylate. Here the latter mixed polymers can be made hydrophilic or even water soluble, by partial salt formation (US-PS 3 305 510, US-PS 3 305 513, US-PS 3 341 505).

Other wound bandage sprays have been described which yield films that can be removed by washing with soap and water. They contain as essential components, mixtures of polyvinyl acetals with copolymers or vinylpyrrolidone and vinylacetate (DT-OS 1 642 063), or plasticized copolymers of vinylacetate and crotonic acid (Fr-PS 2 144 587).

Finally, it is known in connection with compositions that can be sprayed from aerosol containers that the film can be generated on the wound in such fashion that a two-chamber aerosol container is used. Separate portions of softening agent in a volatile organic solvent, and powdered polymers are sprayed on the wounded area either sequentially or simultaneously, from the separate container chambers. After the two substances are mixed and the solvent evaporated, the film is then formed. Here, the polymer should consist of a high proportion of hydroxyalkyl acrylate or methacrylate contained in the mixed polymer, and the softening agent should consist of a polyol, a polyalkylene glycol, or a derivative thereof (US-PS 3 577 516).

A large number of characteristics are required of a film-forming polymer which can be sprayed in solution form, in an easily volatile, non-toxic, organic solvent, and which is to produce a high quality wound bandage. These characteristics can in part be combined only with difficulty, since some of them normally exclude one another.

Thus, the polymer must form a thin, tough, flexible, elastic film on the skin, which adapts very well to all skin movements (even at the joints) without tearing. It must therefore be quite soft, but on the other hand, may not block, since otherwise undesired stickiness easily results in skin creases, especially at temperatures above 35° C. Furthermore, dirt particles may not adhere to the film. Despite its soft, rubberlike character, the film should be resistant to peeling, lest the sprayed bandage be worn off by clothing. Even on rough sections of skin, films generated by spraying must be smooth and impervious. Furthermore, the film should be transparent and colorless so as to be inconspicuous and to afford observation of the wound and of its healing. Also, it must have no unpleasant odor.

In addition to the named mechanical requirements, the polymer must be sufficiently soluble in various solvents which are customarily used for the present purpose. These include ethyl acetate, methylene chloride and/or ethanol or their mixtures with the addition of liquified propellants, such as chlorofluorinated hydrocarbons. The viscosities of these solutions, even at higher solid material content, (up to about 8 weight percent), should be as low as possible in order that the solution be easily sprayable. This means that the required mechanical properties must be obtained with polymers of a relatively low degree of polymerization.

Furthermore, the film produced by the solution must be semipermeable and hydrophilic, in order that moisture given off by the skin, as well as volatile components of the wound secretions can penetrate the film in vapor form, and thus adequate skin breathing is assured. At the same time, the formed film must be insoluble in body fluids and must adhere to the skin under their influence. On the other hand, the hydrophilic character of the polymer must be such that the film formed therefrom can outlast rather short wetting periods during normal washing and bathing without suffering degradation of any kind. Its adherence to acid or alkaline skin surfaces must be so great that the sprayed bandage remains intact without noticeable flaking even on heavily perspiring skin parts, for about three days, under not too great mechanical stress. The film should not discolor on skin, even for longer periods of time, under the influence of light and air. It must resist chemical attack by skin secretions, especially perspiration. Furthermore, it must be toxicologically unobjectionable and not irritate skin. When stored in solution for a longer period of time, the polymer must not decompose, nor may discolorations or milkiness appear. Even after aging for a protracted period, the film-forming substance must remain odor free.

All of these requirements in one polymer are difficult to achieve and were heretofore unachieved until the present invention was made.

Thus, for example, those polymers which contain β-dimethylamino-ethylmethacrylate units or side chains carrying similar amino groups, tend to discolor strongly during production, and especially after aging. Such polymers produce brittle, easily torn films and must be plasticized for the anticipated purpose by adding softening agents. Thus, a danger exists that these softening agents may be partially absorbed by the skin in addition to having a possible irritating effect. This is not an inconsiderable factor from a toxicological point of view. The same is true for the addition of resins which soften and which lend adhesion to such polymers. Occasionally, they too produce allergic reactions on the skin. Using polyvinyl pyrrolidone preparations as wound bandage spray results in films that are much too water soluble. These become sticky under the influence of greater air humidity, such as normally occurs in the areas near the skin. Using poly-2-ethoxy ethyl methacrylate results in products which, after aging, produce an unpleasantly smelling, unclear film. Finally, it should also be mentioned that many of the film-forming polymers or polymer mixtures which have been suggested for use as wound bandage sprays, and which have been described in the patent literature, are not clearly soluble in the usual solvent - propellant mixtures. Hence, when sprayed from an aerosol container, they show an unfavorable, practically unsuitable spray pattern. On the other hand, two-chamber aerosols are too expensive and cumbersome in manufacture as well as in use and yield films which dry too slowly.

The present invention, therefore, is based on the task of creating a polymer for a wound bandage spray, that satisfies the many requirements stated above to the maximum extent possible, and which has none of the cited disadvantages of known polymers or polymer mixtures, and which is excellently suitable for producing a wound bandage in the form of a film-forming, sprayable, stable solution. In particular, the film-forming substance should meet the necessary requirements without addition of auxiliary agents, such as softening agents.

It has been found that this advantageous combination of characteristics can surprisingly be obtained when a mixed polymeride is used for the film-forming, sprayable solution to produce the polymeride for a wound bandage, which is easily manufactured by radical polymerization of relatively simply constructed and economical monomers, namely by mixed polymerization of isobutene with lower acrylic or methacrylic acid esters and maleic acid monoesters.

The subject of the invention is thus a film-forming, sprayable polymeride solution to produce a wound bandage comprising a solution of a copolymer dissolved in a volatile organic solvent. The copolymer comprises:

a. 10 to 30 weight percent isobutene (relative to the total monomer weight);

b. 5 to 85 weight percent of the total monomer weight of one or more esters of acrylic or methacrylic acid with one or more straight-chain or branched monovalent, primary or secondary aliphatic alcohols having one to four carbon atoms;

c. 5 to 85 weight percent of the total monomer weight of one or more maleic acid monoalkyl esters with 1 to 12 carbon atoms in the alkyl moiety.

The maleic acid monoalkyl ester can be replaced wholly or in part by an $\alpha, \beta$ unsaturated monocarboxylic acid, such as acrylic or methacrylic acid, or by basic monomer units containing amino groups, or their mixtures. Alternatively, up to about 75 weight percent of the maleic acid monoester fraction can be replaced by fumaric acid dialkyl ester with one to six carbon atoms in the alkyl residue.

Preferable esters of acrylic or methacrylic acid with straight-chain or branched monovalent, primary or secondary aliphatic alcohols with one to four carbon atoms, or their mixtures, which can be used as component (b) are acrylic acid methyl ester, acrylic acid ethyl ester, acrylic acid n-butyl ester, as well as methacrylic acid methyl ester. The latter is particularly useful when mixed with an acrylic acid ester.

Among the series of maleic acid monoalkyl esters (component c) maleic acid-mono-isopropyl ester, maleic acid-mono-n-butyl ester, maleic acid mono-2-ethylhexyl ester, and maleic acid-mono-n-dodecyl ester, as well as their mixtures, have proven particularly suitable to produce the polymers according to the invention.

Acrylic acid and methacrylic acid are particularly useful as $\alpha, \beta$ unsaturated monocarboxylic acids, which can replace wholly or in part the maleic acid monoalkyl ester in producing the film-forming polymers according to the invention. The alkaline monomer units containing amino groups preferably comprise methacrylic acid-2-dimethyl-amino ethyl ester ($\beta$-dimethyl amino-ethylmethacrylate).

Fumaric acid-di-isopropyl ester, fumaric acid-diethyl ester, and fumaric acid-di-n-butyl ester can be used as fumaric acid dialkyl esters with one to six carbon atoms in the alkyl residue, which can be used up to about 75 weight percent of the maleic acid ester fraction in making the copolymer.

The monomer units with carboxyl or amino groups in the copolymer preferably comprise up to 50 weight percent of the acrylic and/or methacrylic acid ester units.

The exact ratio of the quantity of acrylic or methacrylic acid ester component (component b) and of the maleic acid monoalkyl ester component (component c) or of their monomers, which can replace the maleic acid monoester(s) wholly or in part, can be varied within the limits given supra. The choice of kind and quantity of monomers which are to be copolymerized must be determined in such a way that polymers are obtained which are completely polymerized under normal conditions, and such that they can be easily sprayed in solution with an organic solvent, particularly by means of an added propellant, and that they yield a thin, flexible, elastic, transparent and colorless film on the skin with the advantageous characteristics described above. This choice, however, can easily be determined by a skilled chemist by routine experimentation.

Preparation of the copolymer of this invention is suitably performed in an autoclave with an anchor stirrer. The polymerization temperature is chosen in the range usual for free radical polymerization, preferably between 60° C and 80° C. Known substances for this kind of polymerization such as e.g. azoisobutyric acid dinitrile (AIBN) or benzoyl peroxide. The isobutene is added to excess and simultaneously serves as solvent. The non-converted fraction of isobutene can be removed by venting it after the polymerization reaction is complete. Good results are obtained when about two mol isobutene is added to the monomer mixture, for 1 mol of the sum of acrylic or methacrylic acid esters (component b) and maleic acid monoester (component c). The mol ratio of monomer units in the formed mixed polymeride in this case comes to about two mol acrylic or methacrylic acid ester units, and malic acid monoester units per one mol isobutene units. This corresponds to a fraction of about 20 to 25 weight percent isobutene units, in addition to 75 to 80 weight percent of the sum of acrylic or methacrylic acid ester units and maleic acid monoester units.

In order to keep the reaction substance in stirrable condition while the polymerization reaction is going on, it is recommended, for some formulas, that a small amount of acetic acid ethyl ester or methylene chloride be added after about 3 hours reaction time to the reaction mixture, as an additional solvent in the autoclave (reaction pressure: 6–8 atm at 60°–65° C reaction temperature). After a reaction time of about 5 hours, a small amount of initiator can still be added to accelerate the polymerization. The reaction is complete after about 12 hours. Then, the excess isobutene is evaporated and recovered for subsequent reactions.

The relative viscosities of 1% solutions of copolymers obtained in this way, in toluol at 25° C, have measured values between 1.300 and 1.570 and are relatively low. The values are dependent of the composition of the monomer mixture as well as the chosen reaction conditions. The resulting mixed polymers are readily soluble in toluene, benzene, methylene chloride, acetone, acetic acid ethyl ester, and/or ethanol, and their mixtures with the benzene. Surprisingly, the addition of regulators such as tetrabromethane, mercaptans, or the like, to the monomer mixture, to obtain relatively low levels of polymerization is not required, in contrast to the situation prevailing in the production of known copolymers for the same purpose. These additives are not required to perform the described polymerization in autoclaves and are also undesirable from toxicological points of view. Isobutene as such already has sufficient control effect for the anticipated purpose.

Copolymers are known which are produced by free radical polymerization of isobutene with acrylates or methacrylates. According to the type and amount of the acrylic or methacrylic acid ester used, products with different characteristics are obtained. These can be wax-like, adhesive or non-adhesive, and tough-elastic. For example, the copolymer of methyl acrylate and isobutene (with an isobutene content of 25 weight percent) is quite soft and has a rubber-like elasticity which is favorable for the anticipated purpose. But it has the disadvantage of blocking behavior, which is exhibited when a film produced from such a polymer is used on the skin. This results in dirt particles being held fast, and in the film surface strongly sticking together in creases of the skin.

It could not be foreseen, and therefore was surprising, that adding a fraction of lower maleic acid monoalkyl esters to the monomer mixture prior to polymerization (preferably up to 50 weight percent, for lower ones up to 20 weight percent) results in a polymer which yields a thin, colorless, soft, and flexible film on the skin. In addition to favorable rubber-like elastic characteristics, this film no longer blocks. Even when moisture is present, it adheres excellently to the skin without creating a feeling of tension. Because of its semipermeable, hydrophilic character, it makes possible ready diffusion of water vapor as well as adequate skin respiration. Such films, according to the invention, resist short stresses when washing with soap and water without a tendency to flake, and without other reductions in quality. They are colorless and odorless and remain so even after being carried for protracted periods on the skin. In addition, they resist peeling quite well. The free carboxyl groups in the polymeride effect a weakly acidic character in the spray wound bandage, which has a beneficial effect on antiseptic properties.

By neutralizing a part or all of the free carboxyl groups in the mixed polymeride with amino alcohols, such as e.g. 2-methyl-2-amino-propandiol-1,3 or amines carrying similar hydroxyl groups, the hydrophilic character can be increased even more, should this be desirable for special applications. No discolorations occur in this way.

The solution of the polymer in an easily volatile, nontoxic, organic solvent, to produce the sprayable polymer solution is done in familiar fashion and offers no difficulties. The concentration of the copolymer in the solution should be about 1 to 8 weight percent, preferably 4 to 6 weight percent. Here, the term "solvent" includes the volatile, organic solvent referred to supra to dissolve the polymer as well as a liquid propellant, which is preferably added to the solution and which is miscible with actual solvent.

The relatively highly concentrated polymer solution, which is obtained by dissolving the copolymer can be charged into an aerosol container, together with a propellant in the form of liquified propellant gas, such as a halogen hydrocarbon, and other solvents. It is preferably used commercially in this form. Some special mixed polymers are also easily soluble in ethanol-halogen hydrocarbon propellant mixtures. The ethanol content of such mixtures can be suppressed to about 5 weight percent without precipitation of the polymer occuring. In addition to nitrogen, carbon dioxide or dinitrogen monoxide, the following find good use as propellant gases: trichloromonofluoromethane, dichlorodifluoromethane, dichlorotetrafluoroethane, and especially their mixtures. For the practical application of producing a wound bandage, such polymer solutions are preferably used which have a content of film-forming copolymers between 4 and 8 weight percent relative to the total mixture, including propellants. Lower contents of film-forming mixed polymers generally yield films that are too thin. At higher concentrations, the spray pattern is unfavorably influenced during the spraying process. In addition to the preferred film formation by spraying the polymer solution from an aerosol container, it can also be applied to the skin by a spray container with a compressed rubber ball, or by painting on. For this type of application to the skin, there are many possibilities. The wound bandage spray according to the invention, especially serves to cover small surface wounds and can furthermore be used for larger, already healing wounds, in place of the traditional wound bandage. The solution can additionally contain blood coagulating, antiseptic, or bacteriostatic substances and/or aromatic materials (odorants) that are non-irritating to the skin.

The following examples are provided to more clearly point out the present invention. They are in no way meant as limiting the invention, however.

EXAMPLE 1

A mixture of 464.9 g acrylic acid methyl ester (5.4 mol), 30.0 g methacrylic acid methyl ester (0.3 mol) and 47.5 g maleic acid monoisopropyl ester, to which 3.0 g azoisobutyric acid dinitrile (AIBN) was added, were placed in a stirring autoclave of 2 liter capacity. The autoclave was equipped with an anchor stirrer and with mantle heating. The apparatus was first carefully flushed with nitrogen in order to remove remaining oxygen. Afterwards, 673 g isobutene (12 mol) were pumped into the autoclave and the reaction mixture was heated to 60° C.

After polymerization was initiated, the temperature in the autoclave rose to 63° C. The pressure in the autoclave was 5–6 atm at the beginning of polymerization, and during the reaction it rose to about 8–9 atm. After a reaction time of 4½ hours, a solution of 2.0 g AIBN in 50 g ethyl acetate was forced into the autoclave. After another 2 hours, the same amount of initiator solution was again added. After a total of 12 hours, polymerization was complete. Excess isobutene was vented at about 60° C, and was recovered for further formulations. The reaction product was treated with ethyl acetate and the resulting solution was removed from the autoclave through a valve at its bottom. The relative viscosity of the resulting copolymer in 1% toluene solution at 25° C was 1.349. CH analysis on the polymer produced in the described manner showed a content of about 21 to 25 weight percent of isobutene units.

Various aerosol compositions, intended for filling aerosol containers, were produced with the resulting copolymer. In addition to ethyl acetate, methylene chloride was also used as solvent. When the mixture contained solid materials between 4 and 8 percent, a good spray pattern was obtained, corresponding to the intended use. The aerosol compositions with various liquified chlorofluoridated hydrocarbons and their mixtures, to which usual additives such as antiseptics can be added, are stable against aging. The films resulting by spraying this material on the skin and by evaporation of the solvent, caused no kind of skin irritation, had the above described desirable good mechanical properties, adhered well, showed no change of any kind after brief washing with warm soap solution and remained colorless and odorless after being carried for some time on the skin. Even when usual additives, such as antiseptics, were added to the mixtures, the properties of the film produced therefrom were not changed negatively. If the film is desired to be more hydrophilic, neutralization with an amino alcohol proves useful.

EXAMPLE 2

A formula with the following ingredients were polymerized in the manner described in example 1:

| | |
|---|---|
| acrylic acid methyl ester | 464.9 g (5.4 mol) |
| maleic acid-mono-n-butyl ester | 103.3 g (0.6 mol) |
| isobutene | 673.0 g (12 mol) |
| azoisobutyric acid dinitrile (AIBN) | 7.0 g |
| ethyl acetate (solvent for AIBN) | 100.0 g |

The resulting copolymer contained 23 to 25 weight percent isobutene (relative viscosity: 1.324). After partial neutralization of the free carboxyl groups of the polymer with 2-amino-2-methyl-propandiol-1,3 (at least 50% of the free carboxyl groups of the mixed polymeride should be neutralized), the polymer was fully soluble even in ethanol-halogen hydrocarbon mixtures, and could be sprayed well from aerosol containers.

The mechanical properties, adhesion and age resistance of the film produced from this mixed polymeride were nearly identical to those described according to Example 1.

EXAMPLE 3

A monomer mixture of the following composition was polymerized as described in Example 1:

| | |
|---|---|
| acrylic acid methyl ester | 490.7 g (5.7 mol) |
| maleic acid-mono-isopropyl ester | 47.5 g (0.3 mol) |
| isobutene | 673.0 g (12 mol) |
| AIBN | 7.0 g |
| ethyl acetate | 100.0 g |

The resulting copolymer contained 23 to 25 weight percent isobutene. The relative viscosity of a 1% solution of the polymer in toluene at 25° C was 1.451.

Properties of the film produced from this polymer were quite similar to those described in example 1.

EXAMPLE 4

A monomer mixture of the following compositions was polymerized as described in Example 1:

| | |
|---|---|
| acrylic acid methyl ester | 413.2 g (4.8 mol) |
| methacrylic acid methyl ester | 114.1 g (1.14 mol) |
| acrylic acid | 5.5 g (0.06 mol) |
| isobutene | 673.0 g (12 mol) |
| AIBN | 7.2 g |

Deviating from example 1, in this formulation 50 g of the monomer mixture of acrylic acid methyl ester, methacrylic acid methyl ester and acrylic acid were retained, and 4.8 g of the cited amount of AIBN were dissolved in it. After polymerization was started by addition of 2.4 g of the initiator, 27.4 g of the above described initiator solution was added to the reaction mixture after each 4½ hours of reaction time. In this way, the addition of a further solvent could be avoided. The reaction mixture became a viscous liquid towards the end of the reaction and partial precipitation occurred. The reaction product did, however, remain capable of being stirred. The pressure rose from 6 to 9 atm during the reaction. After the excess isobutene was vented and recovered, the polymer could be dissolved in a solvent to facilitate its being carried off. The solvents include ethyl acetate, methylene chloride or their mixtures. Ethyl acetate/ethanol mixtures were equally useful.

The relative viscosity of a 1% solution of the copolymer in toluene at 25° C was 1.570.

The polymer formed films with properties that were similar to those cited in example 1, but somewhat harder. They could be made softer by adding to the mixture skin-care agents, primarily lanolin alcohols, and thus could be adapted for the requirements of a high quality wound bandage.

EXAMPLE 5

A monomer mixture of the following composition was polymerized as described in example 1:

| | |
|---|---|
| acrylic acid methyl ester | 348.7 g (4.05 mol) |
| methacrylic acid methyl ester | 165.2 g (1.65 mol) |
| methacrylic acid-2-dimethyl-aminoethyl ester | 47.2 g (0.3 mol) |
| isobutene | 673.0 g (12 mol) |
| AIBN | 7.2 g |
| ethyl acetate | 100.0 g |

The relative viscosity of a a1% solution of the copolymer obtained according to this example was about 1.539 in toluene at 25° C.

The polymer formed a weakly alkaline film on the skin. It adhered well and had good mechanical properties. The alkaline character of the copolymer could be removed by adding an acid such as a small amount of benzoic acid. Thus the adhesion of the film was not appreciably reduced.

A composition that could be sprayed from aerosol containers was produced according to the following recipe:

5.0 g copolymer
10.0 g methylene chloride (dichloromethane)
35.0 g ethyl acetate
0.05 g antiseptic (2,4,4'-trichloro-2'-hydroxy-diphenyl-ether)
50.0 g mixture of trichloro monofluoro methane and dichloro difluoro methane (Freon 11/12) in the ratio 50:50
0.008 g odorant (tonalid)

To produce the wound bandage spray, the polymer was dissolved with stirring in the solvent mixture of methylene chloride and ethyl acetate. The antiseptic and deodorant were then added to the solution, and stirring was continued until everything was dissolved. After filtering, the solution was charged into an aerosol container, which was then equipped with a valve head, and was sealed gas tight. A propellant gas comprising trichloromonofluoromethane and dichlorodifluoromethane was then filled into the aerosol container under pressure, through the valve in the valve head (pressure fill procedure).

EXAMPLE 6

A monomer mixture of the following composition was polymerized in the manner described in example 1:

| | |
|---|---|
| acrylic acid ethyl ester | 420.5 g (4.2 mol) |
| maleic acid-mono-isopropyl ester | 284.7 g (1.8 mol) |
| isobutene | 673.0 g (12 mol) |
| AIBN | 7.0 g |
| ethyl acetate | 100.0 g |

The reaction was started with 3 g azoisobutyric acid dinitrile (AIBN). After 4 and 6 hours reaction time, aliquots of 2 g AIBN dissolved in 50 g acetic acid ethyl ester, were added to the reaction mixture. Total reaction time was 20 hours.

The relative viscosity of a 1% solution of the copolymer obtained in this way was 1.290, in ethyl acetate at 25° C.

The polymer was readily soluble in ethyl acetate, acetone, methylene chloride, and after partial neutralization with 2-amino-2-methyl-propandiol-1,3, was also soluble in ethanol and mixtures of ethanol and liquified chlorofluoridated hydrocarbons.

EXAMPLE 7

A monomer mixture of the following composition was polymerized as described in Example 6:

| | |
|---|---|
| acrylic acid-n-butyl ester | 499.9 g (3.9 mol) |
| maleic acid-mono-isopropyl ester | 332.1 g (2.1 mol) |
| isobutene | 673.0 g (12 mol) |
| AIBN | 7.0 g |
| ethyl acetate | 100.0 g |

The relative viscosity of a 1% solution of the resulting copolymer was 1.258 in ethyl acetate at 25° C.

The polymer had similar solubility properties as that produced according to example 6. It was insoluble in toluene and benzene.

EXAMPLE 8

A monomer mixture of the following composition was polymerized in accordance with example 6:

| | |
|---|---|
| acrylic acid methyl ester | 279.8 g (3.25 mol) |
| methacrylic acid methyl ester | 150.2 g (1.5 mol) |
| maleic acid-mono-n-dodecyl ester | 71.1 g (0.25 mol) |
| isobutene | 561.0 g (10 mol) |
| AIBN | 7.0 g |
| ethyl acetate | 100.0 g |

The relative viscosity of a 1% solution of the resulting polymer was 1.360 in toluene at 25° C.

The polymer was soluble in ethyl acetate, methylene chloride, toluene and their mixtures with benzene, and the usual liquified propellants, but was insoluble in ethanol.

EXAMPLE 9

A monomer mixture of the following composition was polymerized in the manner described in example 1:

| | |
|---|---|
| acrylic acid methyl ester | 241.1 g (2.8 mol) |
| acrylic acid ethyl ester | 40.0 g (0.4 mol) |
| maleic acid-mono-2-ethyl-hexyl ester | 182.6 g (0.8 mol) |
| isobutene | 449.0 g (8 mol) |
| AIBN | 3.6 g |
| ethyl acetate | 50.0 g |

The reaction was started with 1.8 g of initiator. After a reaction time of 6 hours, a solution of 1.8 g azoisobutyric acid dinitrile (AIBN) in 50 g acetic acid ethyl ester was forced into the autoclave. The pressure in the autoclave rose from 6.8 atm to 8.3 atm during the reaction. Total reaction time was 20 hours.

The resulting copolymer was soluble in ethyl acetate, acetone and ethanol. For filling aerosol containers, it could be processed with a mixture having an ethanol fraction of only 5%, the remaining 95% consisting of liquified propellant (mixture of chlorofluoridated hydrocarbons). A composition which was sprayable from aerosol containers could also be produced according to the following recipe in the manner described in example 5:

10.0 g copolymers
90.0 g ethanol
100.0 g mixture of trichloro monofluoro methane and dichloro difluoro methane (Freon 11/12) in the ratio of 40:60.

EXAMPLE 10

A monomer mixture of the following composition was polymerized as described in example 1:

| | |
|---|---|
| acrylic acid methyl ester | 275.5 g (3.2 mol) |
| maleic acid-mono-2-ethyl hexyl ester | 182.6 g (0.8 mol) |
| isobutene | 449.0 g (8 mol) |
| AIBN | 5.4 g |
| ethyl acetate | 100.0 g |

The reaction was started with 1.8 g AIBN. After reaction times of 4 and 6 hours, aliquots of 1.8 g of initiator in 50 g ethyl acetate was each time charged into the autoclave. The initial autoclave pressure of 7.0 atm, rose to 8.5 atm during the reaction. Total reaction time was 20 hours.

The copolymer so obtained was soluble in ethyl acetate, acetone and ethanol. For filling into aerosol containers, it could be processed with an ethanol fraction of only 5% with the remaining 95% consisting of liquified propellant (mixture of chlorofluoridated hydrocarbons). A further composition which could be sprayed from aerosol containers is produced according to the following recipe in the manner described in example 5:

5.0 g copolymer
45.0 g ethanol
0.05 g antiseptic
50.0 g mixture of trichloro monofluoro methane and dichloro difluoro methane (Freon 11/12) in the ratio 50:50
0.0008 odorant

EXAMPLE 11

A monomer mixture of the following composition was polymerized as described in example 1:

| | |
|---|---|
| acrylic acid methyl ester | 300.0 g (3.5 mol) |
| maleic acid-mono-2-ethyl hexyl ester | 150.0 g (0.7 mol) |
| fumaric acid-di-isopropyl ester | 150.0 g (0.75 mol) |
| isobutene | 561.0 g (10 mol) |
| AIBN | 5.0 g |
| ethyl acetate | 50.0 g |

The reaction was started with 3.0 g AIBN. After a reaction time of 5 hours, a solution of 2.0 g of the initiator in 50 g ethyl acetate was charged into the autoclave. The initial autoclave pressure of 5 atm rose to 7 atm during the reaction. Total reaction time was 20 hours.

The copolymer so obtained was readily soluble in ethanol. The relative viscosity of a 1% solution of the resulting copolymer was 1.271 in toluene at 25° C.

By simply testing the ratio of solvent or solvent mixture and the propellant composition, good spray behavior, well adapted to the intended purpose can be obtained in all cases. Since the viscosities of the polymer solution are quite low, no undesirable thread formation occurs during spraying. The aerosol mixtures are completely clear, storage proof solutions. The advantage of the films obtained on the skin by one or more sprayings with intermediate drying periods, lies in their very short drying time, even if ethanol and ethyl acetate are used. The films do not block, nor do they show a tendency to stick in skin creases and are resistant to soap alkali. Even short, warm showers or tub baths do not attack the film. Nevertheless, perspiration and wound secretion vapors can penetrate the film without dissolving it. The film does not attract dirt and adheres for several days as a dense, flexible and elastic layer of skin. Eventually it begins to flake off with increasing repulsion of epithelial cells. It does this quickly and without leaving debris. The films remain colorless and odor free even when carried for long periods of time. Besides their use to cover cuts, abrasions and healing surgical wounds, they can also be used to cover salve applications to protect clothing, as well as to cover other kinds of medical preparations applied to the skin.

What is claimed is:

1. A film forming, sprayable solution for forming a wound bandage which comprises a copolymer dissolved in a volatile organic solvent, said copolymer comprising between about 1 and 8 percent by weight of the solution, said copolymer further comprising:
    a. 10–30 percent by weight of total monomers of isobutene,
    b. 5–85 percent by weight of total monomers of 1 or more esters of acrylic or methacrylic acid with straight chain or branched, monovalent, primary or secondary aliphatic alcohols having 1 to 4 carbon atoms, or their mixtures, and
    c. 5 to 85 percent by weight of the total monomers of at least one maleic acid monoalkyl ester having 1 to 12 carbon atoms in the alkyl moiety.

2. The solution of claim 1 wherein said volatile organic solvent is selected from the group consisting of acetic acid ethyl ester, benzene, methylene chloride, ethanol, acetone and mixtures thereof.

3. The solution of claim 1 further comprising a liquefied propellant gas miscible with the organic solvent and wherein the copolymer comprises between about 1 to 8 percent by weight of the solution containing the liquefied propellant gas.

4. The solution of claim 3 in which the liquefied propellant gas is a halogen hydrocarbon or a mixture of different halogen hydrocarbons.

5. The solution of claim 1 in which the copolymer is present in a concentration of 4 to 6 percent by weight, based on the weight of the solution.

6. The solution of claim 1 in which the monomer units with carboxyl groups in the copolymer comprise up to 50 percent by weight of said acrylic and/or methacrylic acid ester units.

7. The solution of claim 1 in which the free carboxylic groups in the copolymer are at least partially reacted with an amino alcohol.

8. The solution of claim 1 which further comprises a blood coagulating antiseptic substance, a deodorant, or both.

* * * * *